(12) United States Patent
Ratke et al.

(10) Patent No.: US 9,283,293 B2
(45) Date of Patent: Mar. 15, 2016

(54) PASTEURIZER WITH CONTROLLED SPRAYER OUTPUT

(75) Inventors: Andre Ratke, Waltrop (DE); Thomas Stienen, Unna (DE)

(73) Assignee: KHS GmbH, Dortmund (DE)

( * ) Notice: Subject to any disclaimer, the term of this patent is extended or adjusted under 35 U.S.C. 154(b) by 569 days.

(21) Appl. No.: 13/580,708

(22) PCT Filed: Mar. 23, 2011

(86) PCT No.: PCT/EP2011/001427
§ 371 (c)(1),
(2), (4) Date: Aug. 23, 2012

(87) PCT Pub. No.: WO2011/141088
PCT Pub. Date: Nov. 17, 2011

(65) Prior Publication Data
US 2013/0004638 A1  Jan. 3, 2013

(30) Foreign Application Priority Data
May 12, 2010  (DE) .......... 10 2010 020 429

(51) Int. Cl.
*A23L 3/02* (2006.01)
*A61L 2/22* (2006.01)
*A23L 3/00* (2006.01)
*A23L 3/04* (2006.01)
*A61L 2/24* (2006.01)

(52) U.S. Cl.
CPC . *A61L 2/22* (2013.01); *A23L 3/003* (2013.01); *A23L 3/04* (2013.01); *A61L 2/24* (2013.01); *A61L 2202/23* (2013.01)

(58) Field of Classification Search
CPC .......... A23L 3/04; A23L 3/02; A23B 4/0056; A23B 55/02; A23B 55/14; A23B 55/18
USPC ................. 426/521, 524, 397, 392, 407, 410; 99/275
See application file for complete search history.

(56) References Cited

U.S. PATENT DOCUMENTS

| | | | |
|---|---|---|---|
| 4,441,406 A | 4/1984 | Becker et al. | |
| 4,568,369 A * | 2/1986 | Destruhaut | ....................... 62/64 |
| 4,693,902 A | 9/1987 | Richmond et al. | |
| 4,704,958 A | 11/1987 | Braymand | |
| 4,849,235 A * | 7/1989 | Braymand | .................... 426/232 |

(Continued)

FOREIGN PATENT DOCUMENTS

| | | |
|---|---|---|
| DE | 10 2005 028195 | 12/2006 |
| EP | 0169361 | 1/1986 |

(Continued)

*Primary Examiner* — Drew Becker
*Assistant Examiner* — Luana Z Long
(74) *Attorney, Agent, or Firm* — Occhiuti & Rohlicek LLP

(57) ABSTRACT

A method for pasteurizing a continuous product chain in a device having an inlet, heat-up, pasteurization, and cooling regions all divided into treatment zones, and a transporter for passing products through these regions includes heating up, pasteurizing, and cooling by heat transfer between the products and a spray medium with which the products are sprayed, for each of the treatment zones, adapting a temperature of the spray medium to cause a desired consequence to heat transfer in the treatment zone, and varying a pasteurization process by changing a volumetric flow rate of the spray medium in at least one treatment zone between a maximum value and a minimum value.

18 Claims, 2 Drawing Sheets

(56) References Cited

U.S. PATENT DOCUMENTS

| | | | |
|---|---|---|---|
| 5,505,054 A * | 4/1996 | Loibl et al. | 62/63 |
| 5,630,321 A * | 5/1997 | Miller | 62/63 |
| 6,834,473 B2 | 12/2004 | Wiedemann | |
| 7,464,559 B2 * | 12/2008 | Chu et al. | 62/171 |
| 7,644,654 B2 * | 1/2010 | Nielsen et al. | 99/453 |
| 2002/0073652 A1 | 6/2002 | Wiedemann | |
| 2002/0170440 A1 | 11/2002 | Wakabayashi et al. | |
| 2003/0049356 A1 * | 3/2003 | Nielsen et al. | 426/522 |
| 2006/0185372 A1 * | 8/2006 | Conde Hinojosa | 62/64 |
| 2007/0082100 A1 | 4/2007 | Dhruv et al. | |
| 2010/0151102 A1 * | 6/2010 | Nielsen et al. | 426/521 |

FOREIGN PATENT DOCUMENTS

| | | |
|---|---|---|
| EP | 89 911 538 | 7/1991 |
| WO | WO 2008/093367 | 8/2008 |
| WO | WO 2008/095576 | 8/2008 |

\* cited by examiner ial phase under 35 USC 371 of
PASTEURIZER WITH CONTROLLED SPRAYER OUTPUT

CROSS REFERENCE TO RELATED APPLICATION

This application is the national phase under 35 USC 371 of international application no. PCT/EP2011/001427, filed Mar. 23, 2011, which claims the benefit of the priority date of German application no. 10 2010 020 429.3, filed May 12, 2010. The contents of the aforementioned applications are incorporated herein in their entirety.

FIELD OF DISCLOSURE

The invention relates to a device and a method for treating objects with liquid, in particular to a pasteurizer and a method for operating such a pasteurizer.

BACKGROUND

Delicate products, i.e. products which tend to perish quickly, for example including liquids such as milk or beer, are made to be long-lasting by means of pasteurization, that is to say by heating above a certain limit temperature, wherein harmful germs contained in the product or liquid are killed during the pasteurization.

In order to achieve a sufficient pasteurization of the filled product to be pasteurized, a certain number of pasteurization units must be administered to this filled product. If this number is not reached, the durability of the product is negatively impaired; if this number is exceeded, the taste of the filled product may be impaired, which is likewise extremely undesirable. The number of pasteurization units is a function of the actual temperature of the product and the time span during which the product is at this actual temperature.

Pasteurizers are generally known. The pasteurizers of interest here are used to pasteurize a continuous product chain. To this end, such a pasteurizer has a heat-up region, a pasteurization region and a cooling region, wherein the products rest on a transport means by which they are transported through the regions in the abovementioned sequence from the inlet to the outlet of the pasteurizer, wherein the products are heated up, pasteurized and cooled in the respective regions.

The transport means is for example a modular belt.

The individual treatment regions are subdivided into zones in the direction of motion of the products.

For the purpose of heat transfer, the products are sprayed from above with a temperature-controlled spray medium, for example water. The spray medium is at different temperatures in the individual zones, the temperature being adapted to the respectively desired type of treatment, i.e. heating up, pasteurization or cooling of the products. For dispensing the spray medium, spray nozzles from which the spray medium exits are arranged above the transport plane of the containers.

In pasteurizers according to the prior art, such as for example that known from EP 89 911 538.0, the open-loop or closed-loop control of such a pasteurizer and also of the pasteurization process takes place in that the conveying speed of the transport means and/or the temperature of the spray medium is changed in at least one treatment zone.

One feature common to all known pasteurizers is that, at least within each individual treatment zone, the volumetric flow rate of the spray medium, measured in cubic meters per hour and square meter of treatment area ($m^3/(h*m^2)$), is either zero—the spray is thus switched off—or else remains constant. It should be noted that, to date, there have been disclosed only pasteurizers in which the volumetric flow rate is the same in all the treatment zones of a pasteurizer.

On account of these circumstances, the known prior art thus suffers from the disadvantage that pasteurizers or the pasteurization process, in the event of changes in the operating state, for example in the event of fault-induced interruptions, fluctuations in the number or products per unit time, etc., can be changed or adapted only by changing the process parameters transport speed and temperature of the spray medium in individual treatment zones, which considerably restricts the possibilities for optimal adjustment or control of the pasteurizer or of the pasteurization process.

SUMMARY

The object of the invention is to remedy and to improve this, so that a pasteurizer or the pasteurization process can be adapted in an improved manner to changed operating states.

To this end, the present invention provides for configuring a pasteurizer in such a way that the volumetric flow rate of the spray medium can also be changed via open-loop or closed-loop control, wherein the volumetric flow rate of the spray medium is always greater than zero. The present invention also provides a corresponding method.

Hereinbelow, the invention will be described on the basis of an example of embodiment.

DETAILED DESCRIPTION

Figure 1:
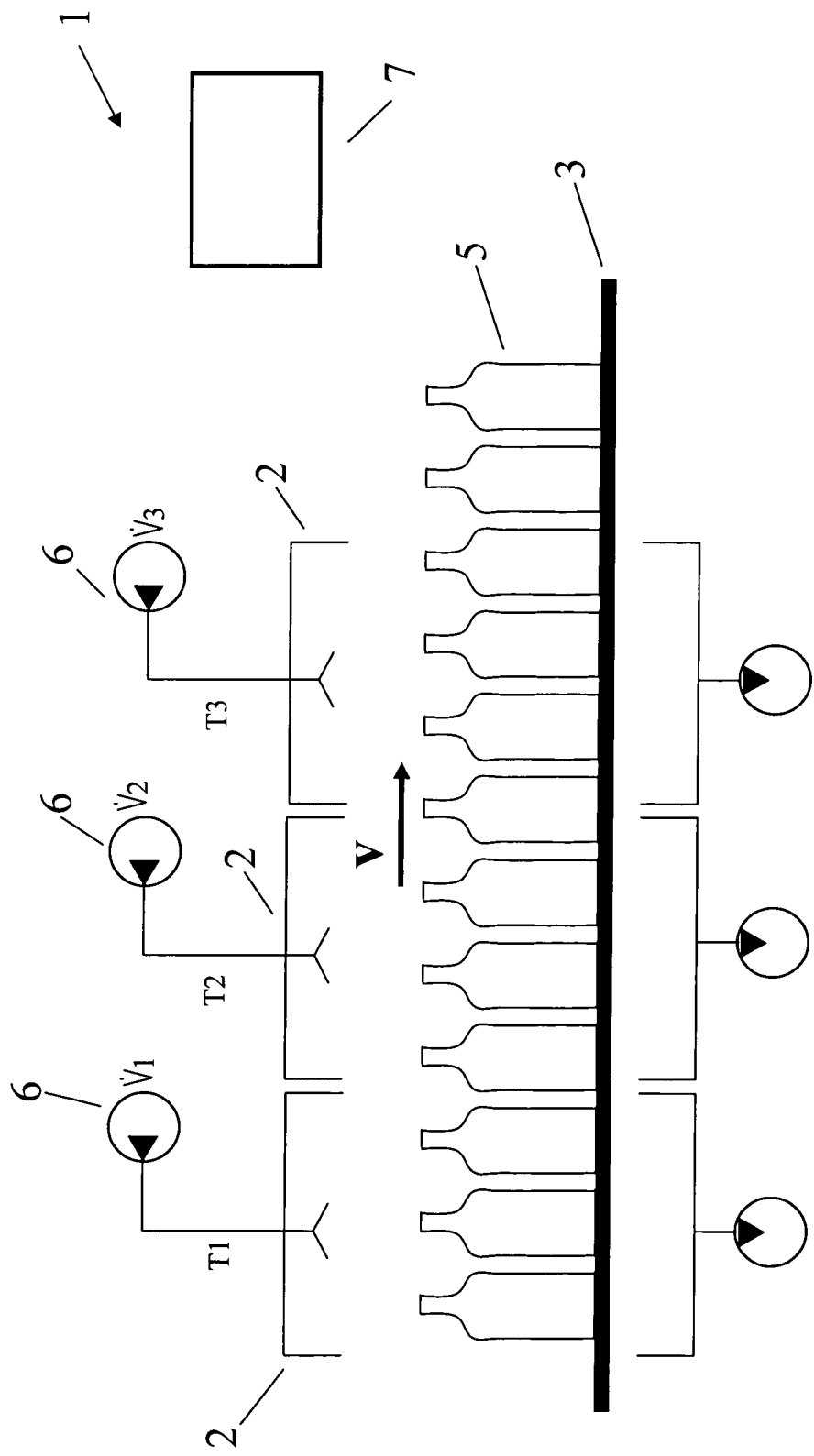
FIG. 1 shows a simplified view of a pasteurizer according to the invention.

In in-house tests carried out by the applicant, it could be found that the heat transfer between a container 5 acted upon by a spray medium and the spray medium is dependent inter alia also on the volumetric flow rate of the spray medium.

It was essentially found that, as the volumetric flow rate of the spray medium increases, there is also an increasing heat transfer between the container 5 and the spray medium.

Furthermore, however, it was also found that there is a lower limit for the volumetric flow rate, below which there is no longer any heat exchange between the container 5 and the spray medium, or no heat exchange that can be mathematically modeled, in particular no heat exchange that can be mathematically predicted.

This lower limit for the volumetric flow rate is represented in simplified form and is reached when the container 5 is no longer constantly fully wetted by the spray medium.

It was also found that there is an upper limit for the volumetric flow rate of the spray medium, above which a further increase in the volumetric flow rate brings no further increase in the heat transfer between the container 5 and the spray medium.

By means of extensive in-house tests carried out by the applicant, it was possible to define parameters, constants and influencing factors on the basis of which the heat transfer between the volumetric flow rate of the spray medium and the container 5 at the maximum useful volumetric flow rate presented above can be mathematically predicted.

By means of further in-house tests carried out by the applicant, it was surprisingly also possible to ascertain that the heat transfer between the spray medium and the container 5 can also be mathematically predicted for those volumetric flow rates lying between the two limit values presented above for the volumetric flow rate of the spray medium.

Due to this discovery, it is now possible for the first time to adapt a pasteurizer or the pasteurization process to changed operating situations not only by varying the parameters transport speed and temperature of the spray medium but also by varying the volumetric flow rate of the spray medium.

At this point, it should be expressly pointed out that it is likewise possible to make such adaptations solely by varying the volumetric flow rate of the spray medium. It is likewise possible, for adapting the pasteurizer 1 or the pasteurization process, to use and to vary the abovementioned and/or further parameters in any combinations.

In order to model the basic mathematical model of the heat transfer between the spray medium and the container 5, it is absolutely necessary to determine, for each type of container to be pasteurized, what heat transfer takes place between this type of container and the spray medium and how this heat transfer changes when for example the container starting temperature T, the temperature of the spray medium T1, T2, T3, the transport speed v and the volumetric flow rate of the spray medium $V°_{1,2,3}$ have different values.

What must be determined, therefore, is the change in the heat transfer between the spray medium and the specific type of container to be pasteurized when one, several or all of the relevant parameters are varied.

If the change in the heat transfer when one or several of the abovementioned or else further parameters are varied for a type of container is known, it is possible to adapt the pasteurization process also by varying the volumetric flow rate $V°_{1,2,3}$ of the spray medium.

Building on the knowledge thus obtained, it is possible to calculate and thus also to monitor the pasteurization process for each individual container 5 during the pasteurization thereof.

To this end, however, it is absolutely essential that the container 5 to be pasteurized, at all times during the pasteurization process, is in such a state in which the heat exchange between the container and the surrounding environment can be calculated with sufficient accuracy and taken into consideration. If the container 5 is at any time not in such a state and thus can exchange heat for example in an uncontrolled manner with its surrounding environment, it is no longer possible to continue calculating the pasteurization process, which results in the risk of undesirable overpasteurization or underpasteurization. Such a situation may arise for example in the event of stoppage of the machine when the container 5 is resting freely on the transport means with the spray medium switched off, wherein all the parameters which define a heat exchange between this container and its surrounding environment, for example ambient temperature, air humidity, flow rate of the air, etc., are not known.

At all times during the pasteurization process, therefore, particularly even in the event of a machine malfunction or break in production, etc., a container 5 to be pasteurized must be exposed to defined ambient conditions so that the heat exchange between the container 5 and its surrounding environment remains able to be calculated.

Finally, it is clear from this prerequisite that the container 5 must be constantly acted upon by a spray medium at a known temperature $T_{1,2,3}$, wherein on the one hand the volumetric flow rate $V°_{1,2,3}$ of the spray medium must also be known and on the other hand the volumetric flow rate $V°_{1,2,3}$ must be at least great enough that the container 5 is constantly fully wetted with spray medium during the spraying process.

In order to calculate the pasteurization process, for each point in time during the pasteurization process the heat transfer between the container 5 and the spray medium is determined, wherein inter alia the starting temperature of the container, the temperature of the spray medium $T_{1,2,3}$, the volumetric flow rate $V°_{1,2,3}$ of the spray medium and for example also the transport speed v of the container are taken into account.

Taking account at least of the time span in which these parameters have unchanged values, the change in temperature of the container 5 and thus also its temperature during the time span and/or its final temperature after the end of the time span are determined, as a result of which the pasteurization units thus administered can also be calculated.

When at least one of the relevant parameters assumes a different value, the calculation is continued using the new values, as a result of which the entire pasteurization process is calculated.

In order to carry out the method according to the invention, a pasteurizer 1 is equipped with sensors which monitor the operating state at least of the pasteurizer 1 and/or at least of part of the overall production system.

By using suitable sensors, such as those that have been known for a long time to a person skilled in the art, information is recorded for example about the degree to which the transport means 3 are occupied by or filled with containers 5, the temperatures $T_{1,2,3}$ of the spray media in the individual treatment zones, the conveying speed v of the transport means 3, etc.

This information is transmitted to a suitable control device 7, for example a device for electronic data processing.

Nominal values and nominal pasteurization procedures for all the relevant products to be pasteurized are preferably also stored in this control device 7.

Also preferably stored in this control device 7 are, for all the relevant types of container or product, all the relevant details regarding the changes in the heat transfer between the container and the spray medium as a function of the relevant parameters.

Furthermore, the control device 7 is connected to appropriate adjusting elements of the pasteurizer 1, such as for example pumps 6, valves, heating elements, drive motors, etc. and is able actively to influence these adjusting elements in terms of their mode of operation or mode of action.

The variation or control of the volumetric flow rate of the spray medium takes place at least in one of the treatment zones, but preferably for all the treatment zones, wherein preferably the volumetric flow rate can be controlled separately via open-loop or closed-loop control for each individual treatment zone.

The volumetric flow rate of the spray medium is preferably produced by process water pumps—hereinafter referred to as hydraulic pumps—which are driven for example by frequency-controlled motors since in this way the volumetric flow rate can be produced and also changed in a particularly energy-saving manner.

The volumetric flow rate can also be influenced by flow control valves and/or bypass lines and/or by spray valves having a variable dispensing volume flow rate.

The volumetric flow rate can also be changed by some of the available spray valves being fully opened or closed via open-loop or closed-loop control.

The open-loop or closed-loop control of the pasteurization process takes place initially in the known manner, according to which the suitable pasteurization program is selected as a function of the product to be pasteurized. As is known from the prior art, the controller of the pasteurizer reacts autonomously to changes in the operating state, which are reported to the controller for example by the sensors or else by active manual interventions by the operating staff, wherein according to the prior art the pasteurization process is adapted to the changed operating state by varying the parameters transport speed v and temperature $T_{1,2,3}$ of the spray media.

As an innovation over this prior art, in a pasteurizer 1 according to the invention the volumetric flow rate $V°_{1,2,3}$ of the spray medium at least in one treatment zone 2 can also be varied. In this case, as a function of the current operating state and knowledge of the changed heat transfer behavior, the controller 7 of the pasteurizer 1 acts on the parameters of the pasteurizer 1 that can be influenced or changed, so that an advantageous adaptation of the pasteurization process to the changed operating state is achieved.

The changes may in this case be influenced by a closed-loop control or else by an open-loop control of the parameters in question, or of the adjusting elements influencing said parameters, that is to say pumps 6, valves, heating elements, drive motors.

The invention will be explained in more detail below on the basis of examples of embodiments.

Example 1

Break in Production

If there is a break in production, i.e. a stoppage of the transport means 3 of the pasteurizer 1, it is absolutely necessary, as discussed at length above, to expose the containers 5 to defined ambient conditions. This requirement in turn requires that the volumetric flow rate of the spray medium in pasteurizers according to the prior art is kept unchanged, which entails considerable energy costs for the constant pumping and temperature control of a considerable volume of the spray medium.

By applying the present invention, it is now possible for the first time to reduce the volumetric flow rate $V°_{1,2,3}$ of the spray medium at least in one of the treatment zones, as a result of which the energy costs can be considerably reduced.

As discussed above, it is possible in this case to reduce the volumetric flow rate $V°_{1,2,3}$ of the spray medium to such an extent that the container is just still fully wetted by the spray medium, without losing the ability to mathematically calculate the pasteurization process.

Example 2

Reduction in Output

If there is a reduced supply of containers 5, it is customary in pasteurizers 1 according to the prior art either to continue to operate the pasteurizer in an unchanged fashion or else to completely switch it off, i.e. not to allow any containers 5 to enter the pasteurizer 1 until there is once again a sufficient number of containers available.

In this case, it is particularly important that the unchanged operation of a pasteurizer 1 when there is a reduced supply of containers leads to the transport means 3 not being fully occupied, which ultimately leads to a reduced degree of efficiency of the overall system and to an increase in the cost per unit of each pasteurized container 5.

By applying the present invention, it is now possible to operate the pasteurizer 1 in a mode in which the transport speed and also the volumetric flow rate $V°_{1,2,3}$ of the spray medium are varied, for example reduced, as a result of which overall a full occupancy of the transport means 3 and a pasteurization process adapted to this reduced transport speed v are possible.

Figure 2:
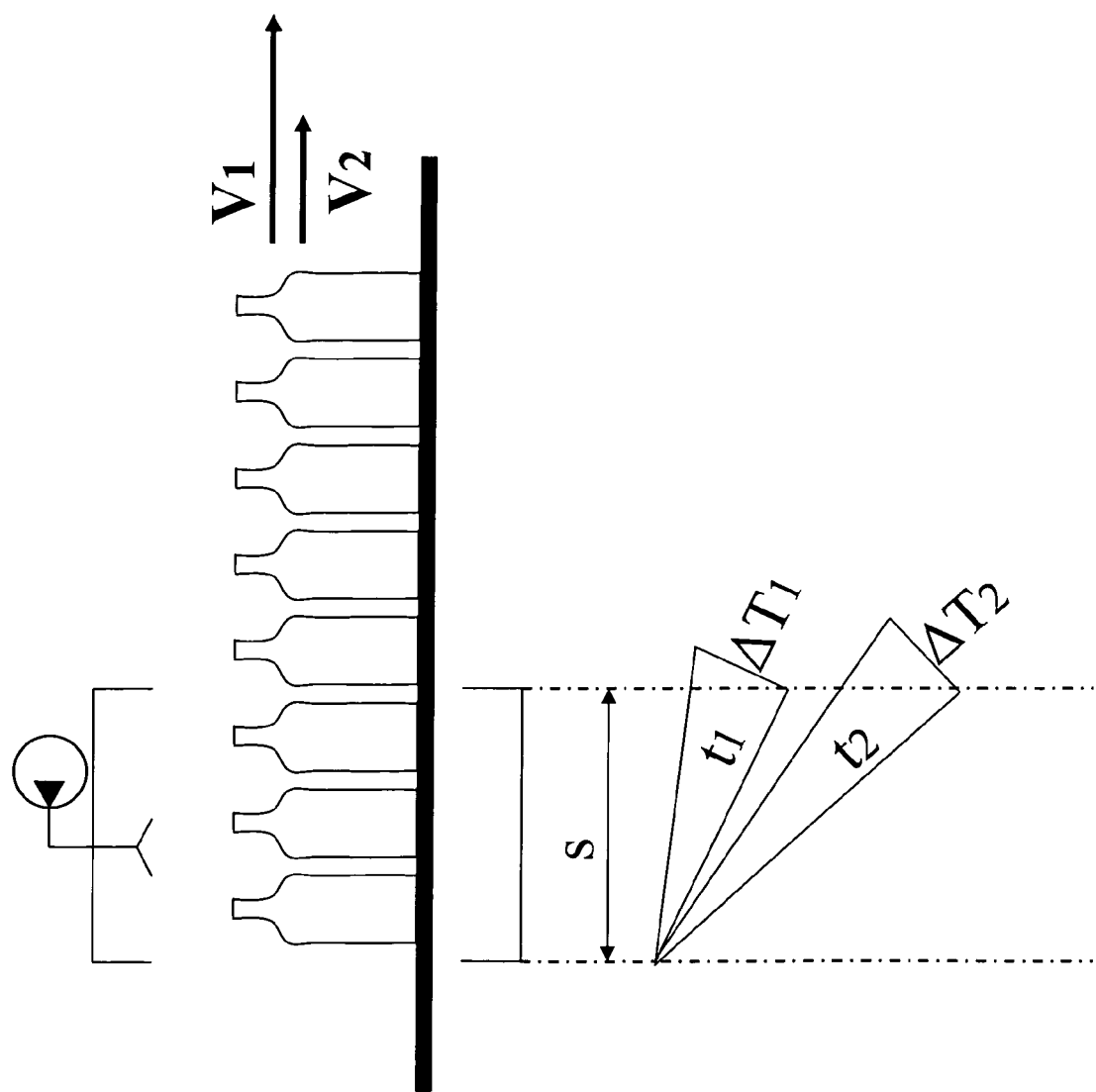
FIG. 2 shows an illustration of a particular operating state of a pasteurizer according to the invention.

This situation is shown in FIG. 2.

If there is a reduced provision of containers 5 upstream of the pasteurizer 1, then according to the invention firstly the speed of the transport means 3 is reduced from the speed $v_1$ to the speed $v_2$, wherein the speed $v_2$ is selected in such a way that the transport means 3 is completely filled with containers 5 even when a reduced number of containers 5 are being provided.

By reducing the transport speed v, the length of time taken to pass through a treatment zone of length s is extended from the time span $t_1$ to the time span $t_2$. In this case, it is essential that the containers 5 at the end of the two time spans $t_1$ and $t_2$ must in each case exhibit the identical temperature change $\Delta t$, since it is provided for the pasteurization process that a certain temperature T is reached at the end of a treatment zone. Consequently, there is a requirement that $\Delta T1 = \Delta T2$.

By virtue of the present invention, the time that is additionally available can now be used to heat the containers 5 more slowly by reducing the volumetric flow rate $V°_{1,2,3}$ of the spray medium, so that the nominal temperature change $\Delta T2$ is achieved in good time but not ahead of schedule, thus making energy savings possible.

Accordingly, it is of course also possible to allow the cooling process that is customary in pasteurization to likewise proceed more slowly.

Analogously it is of course also possible, in the event of an increased inflow of containers, to operate the pasteurizer 1 at an increased speed v, wherein the containers 5 also achieve the nominal temperature change within the now shortened time span due to a suitably increased volumetric flow rate $V°_{1,2,3}$ of the spray medium.

It will be understood here that, instead of a nominal temperature change, the reaching of a nominal temperature may also be provided without departing from the scope of protection of the present invention.

Example 3

Different Types of Container

Due to the operating principle, a pasteurizer 1 can be designed optimally only for one type of container to be pasteurized. However, if it is provided to use such a pasteurizer 1 to pasteurize different types of container, this pasteurizer 1 must necessarily be configured in such a way that even the "container having the greatest heating and cooling requirement and having the poorest heat transfer" can still be reliably pasteurized.

For the pasteurization of other types of container, the pasteurization process according to the prior art is adapted only by varying the parameters transport speed v and temperature $T_{1,2,3}$ of the spray media. Although in a pasteurization process adapted in this way a trouble-free pasteurization of the product is generally still achieved, to this end often an increased outlay on energy is required, which ultimately leads to increased costs per item.

According to the invention it is proposed, in addition to or instead of varying the parameters transport speed v and/or temperature $T_{1,2,3}$ of the spray medium, to vary the parameter volumetric flow rate $V°_{1,2,3}$ of the spray medium in order to adapt an actual pasteurizer 1 or a pasteurization process to different types of container.

In this case, it is particularly advantageous if, for the pasteurization of different types of container, different volumetric flow rates $V°_{1,2,3}$ of the spray medium are provided for each individual one of these different types of container.

By virtue of this procedure it is possible for example to treat a container 5 having a lower heating or cooling requirement and good heat transfer with a lesser volumetric flow rate $V°_{1,2,3}$ of the spray medium compared to a container 5 having a high heating or cooling requirement and poor heat transfer.

This aspect of the invention is particularly important when account is taken of the fact that the size and the conveying speed of a pasteurizer is determined essentially by the diameter of the containers and the desired output of the pasteurizer [containers/hour], since a surface area or footprint for the pasteurizer 1 results from the factors container diameter, number of containers per hour and pasteurization time.

Due to the variation of the volumetric flow rate $V°_{1,2,3}$ of the spray medium, as proposed by the present invention, there is obtained a much greater number of value pairs of the variable parameters for which it is possible to operate a pasteurizer 1 in such a way that the transport means is always fully occupied even for a wide range of different container diameters while precisely adhering to the pasteurization time.

By way of example it may be provided, for a predefined output of the pasteurizer 1, to act upon a small container 5 having a low heating requirement and good heat transfer at a low transport speed v with a low volumetric flow rate $V°_{1,2,3}$ of the spray medium, whereas a large container 5 having a high heating requirement and poor heat transfer is acted upon at a high transport speed v with a high volumetric flow rate $V°_{1,2,3}$ for an identical output.

By virtue of this procedure, overall a full occupancy of the pasteurizer 1 is achieved even with different container diameters, which ultimately leads to low pasteurization costs per container.

Example 4

Gaps in the Product Stream

In certain operating situations, it may happen that the supply of containers 5 to the pasteurizer is completely interrupted for a certain time interval, so that the transport means 3 has an area which contains no containers 5. Due to the mode of operation of a pasteurizer 1, such a gap in the container stream must be moved through the pasteurizer 1 at the same speed v as if the transport means 3 were fully occupied with containers 5. In known pasteurizers 1, the only reaction to such a gap is that the temperature $T_{1,2,3}$ of the spray medium in the respective treatment zone 2 in which the gap is located in each case is lowered by a certain temperature.

According to the invention it is proposed to reduce the volumetric flow rate of the spray medium in the treatment zones 2 in which such a gap is located, or in those treatment zones 2 which contain no containers due to a gap in the container stream.

Due to this reduction in the volumetric flow rate, the costs incurred by heat losses and by producing the volumetric flow rate can be reduced.

It will be understood that the operating situations mentioned in the examples of embodiments and the measures associated with these operating situations—including in the respective combination—are merely examples and do not limit the scope of the present invention. In particular, these examples of embodiments do not limit the scope of the present invention to the effect that said combinations of operating situation and measure must necessarily be retained. Instead, the present invention also extends to other, "1 to 1", "1 to n" and "n to 1" combinations of the aforementioned and further operating situations and measures.

LIST OF REFERENCES

1 pasteurizer
2 treatment zones
3 transport means
4 control device
5 container
6 pump
7 control device
T1, T2, T3 temperature of spray medium
ΔT1, ΔT2 changes in temperature
$V°_{1,2,3}$ volumetric flow rate of spray medium
t1, t2 time spans
s length of treatment zone

The invention claimed is:

1. A method for pasteurizing a continuous product chain in a device comprising an inlet, a heat-up region divided into treatment zones, a pasteurization region divided into treatment zones, a cooling region divided into treatment zones, an outlet, and transport means for passing products through said heat-up region, then through said pasteurization region, and then through said cooling region from said inlet to said outlet of said device, said method comprising heating up, pasteurizing, and cooling by heat transfer between said products and a spray medium with which said products are sprayed, wherein heating up, pasteurizing, and cooling comprises, for each of said treatment zones, adapting a temperature of said spray medium at said treatment zone to cause a desired consequence to heat transfer in said treatment zone, and varying a pasteurization process by changing a volumetric flow rate of said spray medium in said treatment zone between a maximum value and a minimum value, whereby each treatment zone has a volumetric flow rate that is able to be varied in time independently of volumetric flow rates in other treatment zones.

2. The method of claim 1, wherein adapting a temperature of said spray medium comprises changing said temperature of said spray medium.

3. The method of claim 1, further comprising changing a rate at which said transport means passes said products.

4. The method of claim 2, wherein varying said pasteurization process further comprises changing a rate at which said transport means passes said products.

5. The method of claim 1, further comprising selecting one or more volumetric flow rates of said spray medium based at least in part on a type of container whose contents are to be pasteurized.

6. The method of claim 1, further comprising, based at least in part on a determination that, in at least one treatment zone, a volumetric flow rate of said spray medium is at or above a predetermined volumetric flow rate, reducing, in said at least one treatment zone, a volumetric flow rate of said spray medium to be below said predetermined volumetric flow rate of said spray medium at said at least one treatment zone.

7. The method of claim 1, further comprising, based at least in part on a determination that, in at least one treatment zone, a volumetric flow rate of said spray medium is at or below a set volumetric flow rate, increasing, in said at least one treatment zone, a volumetric flow rate of said spray medium to be above a set volumetric flow rate of said spray medium at said at least one treatment zone.

8. The method of claim 1, further comprising reducing a volumetric flow rate of said spray medium and increasing a time span during which said container to be pasteurized is exposed to said spray medium thereby achieving a selected temperature change of said container.

9. The method of claim 1, further comprising increasing a volumetric flow rate of said spray medium and reducing a time span during which said container to be pasteurized is exposed to said spray medium thereby achieving a selected temperature change of said container.

10. The method of claim 1, further comprising, based at least in part on an operating condition of said device, reducing, in at least one treatment zone, a volumetric flow rate of said spray medium.

11. The method of claim 1, further comprising, based at least in part on an operating condition of said device, increasing, in at least one treatment zone, a volumetric flow rate of said spray medium.

12. The method of claim 1, further comprising, within a first treatment zone, changing a volumetric flow rate of said spray medium such that, at a first time, said volumetric flow rate of said spray medium within said first treatment zone has a first value, and at a second time that is different from said first time, said volumetric flow rate of said spray medium within said first treatment zone has a second value, wherein said second value is different from said first value, wherein volumetric flow rate within said treatment zone is time-varying, and wherein said first value and said second value are within a closed interval bounded by a maximum value for said first treatment zone and a minimum value for said first treatment zone, said method further comprising, within a second treatment zone, changing a volumetric flow rate of said spray medium such that, at a third time, said volumetric flow rate of said spray medium within said second treatment zone has a third value, and at a fourth time that is different from said third time, said volumetric flow rate of said spray medium within said second treatment zone has a fourth value, wherein said fourth value is different from said third value, wherein volumetric flow rate within said treatment zone is a function of time, wherein said third value and said fourth value are within a closed interval bounded by a maximum value for said second treatment zone and a minimum value for said second treatment zone, wherein changing volumetric flow rate in said first treatment zone is carried out independently of changing volumetric flow rate in said second treatment zone, and wherein said first treatment zone and said second treatment zone are different treatment zones.

13. The method of claim 1, further comprising determining a heat transfer rate between said spray medium and a container containing a product in response to a change in temperature of said spray medium.

14. The method of claim 1, further comprising determining a heat transfer rate between said spray medium and a container containing a product in response to a change in volumetric flow rate of said spray medium from a first non-zero value to a second non-zero value.

15. The method of claim 1, further comprising controlling heat transfer between a container that contains a product and an environment surrounding said container.

16. The method of claim 1, further comprising detecting a break in production, and, in response to detecting said break in production, reducing a volumetric flow rate in at least one treatment zone from a first non-zero value to a second non-zero value.

17. The method of claim 1, further comprising detecting a reduction in container supply rate and, in response, changing a volumetric flow rate in at least one treatment zone from a first non-zero value to a second non-zero value.

18. The method of claim 1, further comprising detecting a resumption following a break in production, and increasing volumetric flow rate in at least one treatment zone from a first non-zero value to a second non-zero value in response to said detection.

* * * * *